United States Patent [19]

Sethofer

[11] 4,325,830
[45] Apr. 20, 1982

[54] THREE RING DIOXANE LIQUID CRYSTALLINE COMPOUNDS

[75] Inventor: Nicholas L. Sethofer, San Jose, Calif.

[73] Assignee: Timex Corporation, Waterbury, Conn.

[21] Appl. No.: 219,673

[22] Filed: Dec. 24, 1980

[51] Int. Cl.³ .................. C07D 319/04; G02F 1/13; C09K 3/34
[52] U.S. Cl. .................. 252/299.61; 252/299.63; 252/299.5; 260/340.7; 350/350 R; 350/350 S
[58] Field of Search .............. 260/340.7; 252/299.5, 252/299.61, 299.63; 350/350 R, 350 S

[56] References Cited

U.S. PATENT DOCUMENTS

| | | | |
|---|---|---|---|
| 3,947,375 | 3/1976 | Gray et al. | 252/299 |
| 4,062,798 | 12/1977 | Boller et al. | 252/299.61 |
| 4,085,222 | 4/1978 | Rhodes et al. | 424/278 |
| 4,130,502 | 12/1978 | Eidenschink et al. | 252/299.63 |
| 4,154,697 | 5/1979 | Eidenschink et al. | 252/299 |
| 4,181,625 | 1/1980 | Eidenschink et al. | 252/299.63 |
| 4,200,580 | 4/1980 | Hsu | 252/299.61 |
| 4,211,666 | 7/1980 | Inukai et al. | 252/299 |
| 4,273,929 | 6/1981 | Boller et al. | 252/299.61 |
| 4,298,528 | 11/1981 | Sethofer | 252/299.61 |

FOREIGN PATENT DOCUMENTS

| | | | |
|---|---|---|---|
| 2257588 | 6/1973 | Fed. Rep. of Germany | 252/299.61 |
| 139852 | 1/1980 | German Democratic Rep. | |
| 139867 | 1/1980 | German Democratic Rep. | |
| 2044767 | 10/1980 | United Kingdom | 252/299.61 |
| 2063288 | 6/1981 | United Kingdom | 252/299.61 |

OTHER PUBLICATIONS

Sorkin; H., Mol. Cryst. Liq. Cryst. (Letters), vol. 56, pp. 279-281, (1980).
Bata; L., Advances In Liquid Crystal Research and Applications, vol. 2, Proceedings of the 3rd Liq. Cryst. Conf. of Socialist Countries, Budapest, Aug. 21-31, 1979, Pergamon Press, (1981), pp. 997-1002.

*Primary Examiner*—Teddy S. Gron
*Attorney, Agent, or Firm*—William C. Crutcher; Edward J. Timmer

[57] ABSTRACT

Disclosed are compounds of the formula:

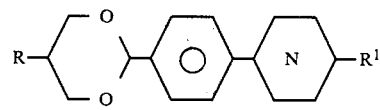

where R is alkyl or alkoxy and $R^1$ is alkyl, alkoxy, cyano or nitro and where ring N is a benzene or saturated cyclohexane ring. The compounds of the invention are compatible and useful in admixture with the general classes of cyanophenyl dioxane and/or cyclohexyl dioxane type liquid crystalline compounds to provide a broad nematic temperature range mixture with advantageous electrooptical and other properties. Novel admixtures including preferably at least about 30 weight percent of the compounds of the invention are disclosed. Preferred admixtures also include at least about 30 weight percent of cyanophenyl dioxanes and at least about 20 weight percent of cyclohexyl dioxanes.

9 Claims, No Drawings

THREE RING DIOXANE LIQUID CRYSTALLINE COMPOUNDS

FIELD OF THE INVENTION

The present invention relates to electrooptical displays to both the twisted nematic and guest-host type and to liquid crystalline materials and admixtures for use in such displays.

DESCRIPTION OF THE PRIOR ART

Previously developed two-ring compounds of the general formulas

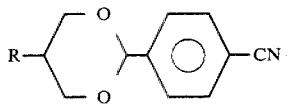

(cyanophenyl dioxanes covered in copending U.S. application Ser. No. 136,855 filed Apr. 3, 1980 in the name of Howard Sorkin and of common assignee herewith) and

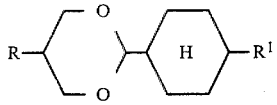

(cyclohexyl dioxanes covered in copending U.S. application Ser. No. 135,381 filed Mar. 28, 1980, now U.S. Pat. No. 4,298,528, of common inventorship and assignee herewith) brought about substantial improvements in liquid crystal display technology in both the fields of field effect, twisted nematic displays using parallel or crossed polarizers and in the fast emerging guest-host technology using guest pleochroic dyes in a host liquid crystal material and eliminating the need for polarizers.

Among the advantages of the cyanophenyl dioxane compounds are extremely high positive values of dielectric anisotropy ($\Delta\Sigma$) which translates into very low electrical threshold and saturation voltages; e.g., about 0.6 V and about 1.4 V, respectively. The compounds, due to their steep electrooptical saturation curve and reported lower temperature dependence, are very suitable in the broad spectra of liquid crystal display applications, including multiplexed displays, low voltage operation, etc. As a result of their relatively low optical birefringence ($\Delta\eta$) values, e.g., about 0.1, the cyanophenyl dioxanes were found very useful for guest-host type display mixtures. The cyclohexane dioxane type compounds, especially those with dialkyl substituents were found to have an extremely low optical birefringence, e.g., $\Delta\eta$ values below 0.05, and still have a positive dielectric anisotropy. These properties are extremely useful in the preparation of mixtures for low voltage/high contrast displays of the guest-host type.

It is well known that most alkyl substituted cyanophenyl dioxane compounds exhibit monotropic phase rather than a nematic phase and that certain quaternary mixtures show a nematic range between 5° C. and 39° C. only. Consquently, to date, two-ringed dioxane compounds like those described hereinabove were used only as additives in mixtures without taking full advantage of their structural and electro-optical properties.

What is still needed, however, are nematic liquid crystalline materials with compatible structural, chemical and electrooptical properties are those described hereinabove, and having broad nematic temperature ranges and high clearing points. Such compatible nematic liquid crystalline compounds in admixture with the aforementioned phenyl and cyclohexyl dioxanes would result in broader range nematic mixtures and better use of desired properties of dioxanes.

Three ring dioxane liquid crystalline compounds of the general formula

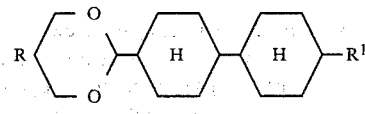

(which are also described in the aforementioned copending U.S. application serial number 135,381, now U.S. Pat. No. 4,298,528) have been found to be useful in admixtures with the two ring cyanophenyl dioxanes and/or cyclohexyl dioxanes described above to provide broader nematic temperature range admixtures which still remain low viscosity and low optical birefringence, e.g., $\Delta\eta=0.05$. These compounds and admixtures containing them are described more fully in a copending U.S. patent application entitled "Cyclohexyl Cyclohexyl Dioxane Liquid Crystal Compounds and Admixtures Containing Same" of common inventorship and common assignee herewith.

Japanese patent application No. 55-85583 published June 25, 1980 and U.K. patent application No. 2,041,354A published Sept. 10, 1980 disclose two and three ring liquid crystalline compounds having the general formula

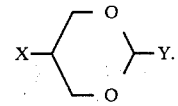

Specific compounds disclosed include

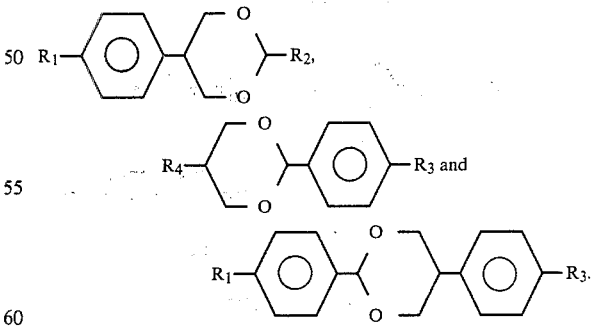

SUMMARY OF THE INVENTION

Accordingly, the present invention provides a new group of compounds having structural, chemical and electrooptical properties compatible with the cyanophenyl and cyclohexyl dioxane class of compounds discussed hereinabove. The new group of compounds exhibits a broad nematic temperature range, high clearing points, positive dielectric anisotropy and relatively low optical birefringence.

Compounds of the invention are represented by the formula:

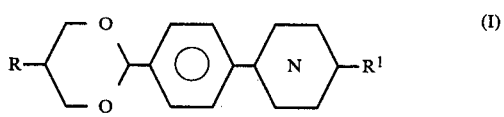

where R is alkyl or alkoxy and $R^1$ is alkyl, alkoxy, cyano or nitro where ring N is a benzene or saturated cyclohexane ring.

The compounds of the invention are characterized by a broad nematic temperature range and high clearing point and are preferably present in liquid crystal admixtures in amounts of at least about 30 weight percent.

Preferred admixtures of the invention include at least about 30 weight percent of compound I, at least about 30 weight percent of cyanophenyl dioxane and at least about 20 weight percent cyclohexyl dioxane.

DESCRIPTION OF PREFERRED EMBODIMENTS

The compounds of the present invention may be prepared as follows:

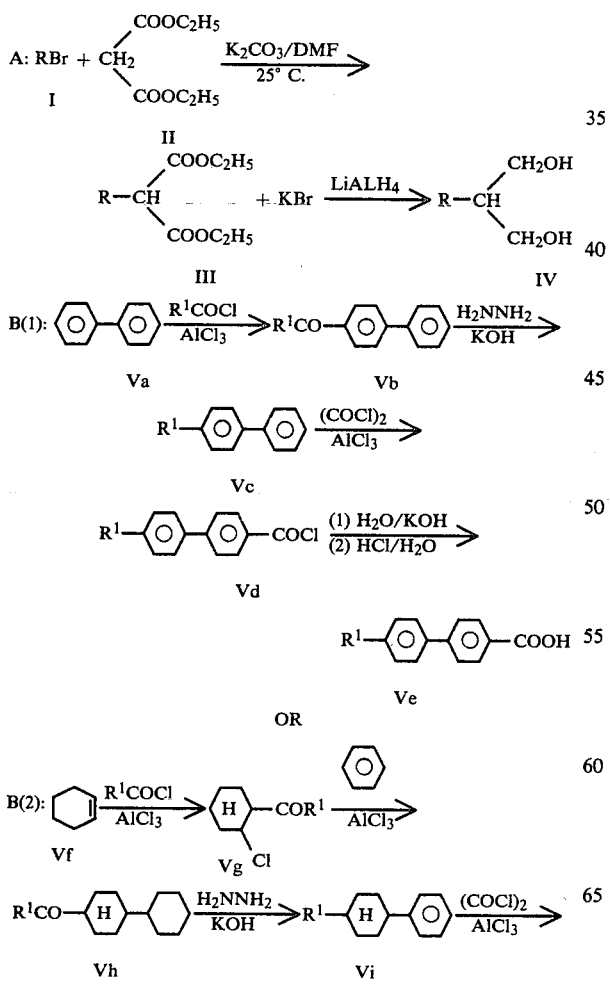

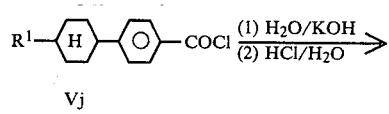

where ring N is as described hereinabove. Compounds I and II were obtained from commercial source (Aldrich Company) and alkylations of malonic acid esters were carried out according to well known methods.

The reduction of the R-substituted malonic acid esters was carried out using lithium aluminum hydride as a reducing agent in diethyl ether.

Compounds V (i.e., alkyl-biphenyl carboxylic acids, alkyl-cyclohexyl-benzoic acids, etc.) were prepared by methods known to those skilled in the art such as Friedel-Crafts acylation, Wolff-Kishner reduction and another Freidel-Crafts reaction with oxalyl chloride and hydrolysis of chloride to carboxylic acid. Preparation of compound Ve involves alkylation of biphenyl via Friedel-Crafts acylation and Wolff-Kishner reduction followed by another Friedel-Crafts acylation with oxalyl chloride. Preparations of compounds Vk were carried out according to modified procedures, described originally by: (1) Johnson, et.al., J. American Chemical Society, Volume 67, No. 7, p. 1045; July 10, 1945, and (2) Neintzescu et.al., Ann., 519,260 (1935). Reduction of the carboxyl groups of compound V to methanols VI was carried out with Vitride reducing agent.

Oxidation to desired aldehydes was achieved with dimethyl sulfoxide, either with $N,N^1$-dicyclohexyl-carbodiimide and pyridinium trifloroacetate or by refluxing the methanol in DMSO, passing the stream of air through the reaction medium.

Resulting dioxane compounds VIII of present invention are obtained as both trans and cis isomers, typically in a better than 3:1 ratio. The isomers can be readily separated by simple crystallization from hexanes, ethyl alcohol or other well known solvents. The trans configuration is the one which presumably accounts for nematic characteristics of the subject compounds.

The following examples illustrate synthetic routes for preparation of compounds of present invention.

EXAMPLE 1

5-propyl-2-(4-(4-heptylcyclohexyl)phenyl)-1,3 dioxane (A) Formation of 2-propyl-1,3 propane diol IV:

To a 3 liter, 3 neck round bottom flask fitted with a condenser for merely precautionary purposes and an air-driven stirrer the following materials are added:
 (1) 150.53 ml (1 mole) of diethyl malonate
 (2) 109 ml (1.2 mole) of n-propyl bromide
 (3) 166 g (1.2 mole) of potassium carbonate
 (4) 400 ml of N,N-dimethyl formamide The reaction mixture is stirred at room temperature until the amount of 2-propyl-1,3 diethyl malonate in the reaction mixture reaches 93 to 95% by gas chromatography, usually in seven days.

Reduction of malonate to diol as been performed by the method described in Fieser & Fieser, Reagents for Organic Synthesis Vol. 1, p. 584, i.e., with lithium aluminum hydride in diethyl ether.

(B) Formation of trans-4(4-heptylcyclohexyl)Benzoic Acid

Introduce approximately 500 ml of hexane into 3-neck flask fitted with air-driven stirrer and thermometer, all fitted into appropriate cooling both. Cool the solvent to $-60°$ C., then add 82.2 g (1 mole) of cyclohexene, 160 g (1.2 mole) of $AlCl_3$, anhydrous, and, 178 g (1.2 mole) of heptanoyl chloride. Stir for $3\frac{1}{2}$ hours while raising temperature slowly to $-40°$ C., then discontinue stirring and decant solvent from thick oily substance. Wash at least once with cold hexane and react 1-heptanone-2-chlorocyclohexane (Vg) with excess of benzene (approximately 500 ml) and additional aluminum chloride-approximately 60 g, i.e., less than 0.5 mole. Stir for $3\frac{1}{2}$ hours with temperature being 45° C. Then cool down to room temperature, pour over water with ice, separate layers, and evaporate excess of benzene. Yield of compound Vh, i.e., 4-heptanoylcyclohexylbenzene is 75 to 80% having a trans/cis isomers ratio of 2.5/1.

Following Wolff-Kishner reduction (Vi), Friedel-Crafts acylation (Vj) and hydrolysis (Vk) are routine type of synthesis steps which are well known to those skilled in the art. Separation of trans/cis isomers is done at the stage of Vk by recrystallization from methanol to achieve pure trans-4(4-heptylcyclohexyl)benzoic acid.

(C) Formation of trans-4-(4-heptylcyclohexyl)benzaldehyde:

Introduce 84 ml (0.3 mole) Vitride reducing agent (e.g. sodium-bis-(2-methoxy-ethoxy)aluminum hydride) and about 250 ml of dry benzene (or toluene) into 3-neck flask fitted with a condenser and air-stirrer and bring to reflux. Add dropwise in a course of 30 minutes a solution of 30 g trans-4(4-heptylcyclohexyl)benzoic acid in benzene and continue to reflux for additional 3-4 hours. Mixture is then cooled to room temperature and introduced slowly with stirring into a 20% aqueous HCl solution plus ice. After addition, the mixture is vigorously stirred for another 20 to 30 minutes and resulting layers are then separated. Evaporation of benzene yielded the desired compound, trans-4-(4-heptylcyclohexyl)benzylalcohol in typically 99.9% purity by gas chromatography and yields over 95%.

Next step, i.e., oxidation of alcohol to aldehyde, was conducted by refluxing of benzylalcohol in 7 M excess of dimethyl sulfoxide with a stream of air, in this particular case for 6 hours. However, when second ring was unsaturated (benzene)- e.g., 4-(4-hexylphenyl)-benzylalcohol, reaction time was close to 25 hours. Reaction progress was monitored on a gas chromatograph.

Compound was extracted from the reaction mixture with methylene chloride, washed with water, solvent evaporated and aldehyde purified via sodium bisulfite complex. The yield was 70% and purity by gas chromatography was 96.9%.

(D) Formation of 5-propyl-2-(4-(4-heptylcyclohexyl)-phenyl)-1,3-dioxane

To a 3-liter, 3-neck round bottom flask fitted with a condenser, Dean Stark trap and air-driven stirrer, the following are introduced:
 (1) 16.54 g (0.14 mole) 2-propyl-1,3 propanediol
 (2) 28.6 g (0.1 mole) trans-4(4-heptylcyclohexyl)benzaldehyde
 (3) 500 ml benzene
 (4) trade p-toluene sulfonic acid.

the mixture is brought to reflux and the water removed azeotropically, reaction time being 6 to 8 hours. Then the mixture was cooled to room temperature, washed with 10% solution of KOH and several times with water, and the layers were separated and benzene evaporated.

The raw compound contained two portions with identical infra-red spectra, i.e., trans-cis isomers in better than 3:1 ratio.

Separation of isomers and purification of desired trans isomer was accomplished by simple crystallization from hexanes and ethyl alcohol. After the final step, no cis isomer was detected.

Transition temperatures for trans-5-n-propyl-24-n-heptylcyclohexyl)phenyl)-1,3-dioxane as measured on Perkin-Elmer DSC-2 were as follows:

C-N (crystal-nematic) = 59.6° C.

N-I (nematic-isotropic) = 145.8° C.

$\Delta H = 4.9$ K cal/mole

Other exemplary compounds have been prepared by the synthesis procedures set forth hereinabove and are listed below along with corresponding properties.

EXAMPLE 2

Trans-5-ethyl-2(4-(4-n-heptylcyclohexyl)-phenyl)-1,3-dioxane

C—N = 67.2° C.

N—I = 128.3° C.

$\Delta H = 4.0$ K cal/mole

EXAMPLE 3

Trans-5-n-pentyl-2(4-(4-n-heptylcyclohexyl)phenyl)-1,3-dioxane

| | |
|---|---|
| $C-S_1$ = 74.3° C. | (crystal to smectic) |
| $S_{1-S2}$ = 95.3° C. | (smectic to smectic) |
| $S_{2-Sc}$ = 110.0° C. | (smectic to smectic) |
| $S_{3-N}$ = 123.0° C. | (smectoc to nematic |
| N-I = 164.0° C. | (nematic to isotropic) |
| $\Delta H$ = 5.36 k cal/mole | |

EXAMPLE 4

Trans-5-ethyl-2-(4-(4-n-pentylcyclohexyl)-phenyl)-1,3-dioxane $C-S_1 = 66.8°$ C.

$S_1-S_2 = 73.8°$ C.

$S_2-N = 79.0°$ C.

$N-I = 140.0°$ C.

$\Delta H = 3.1$ K cal/mole

EXAMPLE 5

Trans-5-n-propyl-2(4-(4-n-pentylcyclohexyl)-phenyl)-1,3-dioxane $C-N = 74.0°$ C.

$N-I = 157.4°$ C.

$\Delta H = 3.5$ K cal/mole

EXAMPLE 6

Trans-5-ethyl-2-(4'-n-hexylbiphenyl)-1,3-dioxane

This compound was prepared as explained above with the exception that in the oxidation of alcohol to aldehyde, compound VI to VII, the reaction time (refluxing of 4-(4-hexylphenyl)-benzylalcohol in 7 m excess of dimethyl sulfoxide with air stream) was extended to about 25 hours with reaction progress monitored on a gas chromatograph.

$C-S = 61.4°$ C.

$S-N = 98.0°$ C.

$N-I = 138.8°$ C.

$\Delta H = 7.6$ K cal/mole

Examples of certain novel eutectic mixtures incorporating compounds of the invention are as follows:

EXAMPLE A

| | MOLE FRACTIONS |
|---|---|
| $C_2H_5$—[dioxane]—[O]—[H]—$C_7H_{15}$ | 0.231 |
| $C_3H_7$—[dioxane]—[O]—[H]—$C_7H_{15}$ | 0.196 |
| $C_2H_5$—[dioxane]—[O]—[H]—$C_7H_{11}$ | 0.323 |
| $C_3H_7$—[dioxane]—[O]—[H]—$C_5H_{11}$ | 0.250 |

$C-N = 36.8°$ C.
$N-I = 141.9°$ C.

EXAMPLE B

| | MOLE FRACTIONS | WEIGHT % |
|---|---|---|
| $C_4H_9$—[dioxane]—[O]—CN | 0.143 | 11.8 |
| $C_5H_{11}$—[dioxane]—[O]—CN | 0.086 | 7.2 |
| $C_6H_{13}$—[dioxane]—[O]—CN | 0.111 | 10.2 |
| $C_7H_{15}$—[dioxane]—[O]—CN | 0.067 | 6.4 |
| $C_2H_5$—[dioxane]—[H]—$C_5H_{11}$ | 0.197 | 17.1 |
| $C_3H_7$—[dioxane]—[H]—$C_7H_{15}$ | 0.035 | 3.5 |
| $C_2H_5$—[dioxane]—[H]—[H]—$C_5H_{11}$ | 0.112 | 12.8 |
| $C_3H_7$—[dioxane]—[O]—[H]—$C_5H_{11}$ | 0.105 | 12.7 |
| $C_2H_5$—[dioxane]—[O]—[H]—$C_7H_{15}$ | 0.086 | 10.7 |
| $C_3H_7$—[dioxane]—[O]—[H]—$C_7H_{15}$ | 0.058 | 7.6 |

$C-N = -40.0°$ C.
$N-I = 83.6°$ C.
$\Delta\eta = 0.08$

EXAMPLE C

| | MOLE FRACTIONS | WEIGHT % |
|---|---|---|
| $C_4H_9$—[dioxane]—[O]—CN | 0.180 | 14.9 |
| $C_5H_{11}$—[dioxane]—[O]—CN | 0.109 | 9.6 |
| $C_7H_{15}$—[dioxane]—[O]—CN | 0.089 | 8.6 |
| $C_2H_5$—[dioxane]—[H]—$C_5H_{11}$ | 0.254 | 22.2 |
| $C_3H_7$—[dioxane]—[H]—$C_7H_{15}$ | 0.052 | 5.1 |
| $C_3H_7$—[dioxane]—[O]—[H]—$C_5H_{11}$ | 0.129 | 15.7 |
| $C_2H_5$—[dioxane]—[O]—[H]—$C_7H_{15}$ | 0.109 | 13.7 |
| $C_3H_7$—[dioxane]—[O]—[H]—$C_7H_{15}$ | 0.078 | 10.2 |

$C-N = -13.2°$ C.
$N-I = 76.7°$ C.
$\Delta n = 0.08$

Note: Eutectic mixtures A, B & C were calculated according to Schroder-van Laar equation programmed to HP9825A computer. Actual transition temperatures were measured in Perkin-Elmer DSC-2.

The general class of cyanophenyl dioxanes useful in admixtures of the invention has the general formula

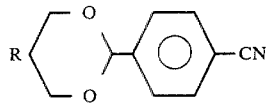

where R is typically alkyl or alkoxy and are described more fully in copending U.S. application Ser. No. 136,855 filed Apr. 3, 1980. An exemplary synethesis of 2-(4-cyanophenyl)-5-n-butyl-1,3-dioxane employed in Examples B and C is as follows:

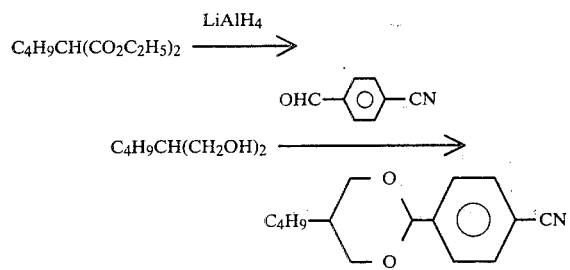

The general class of useful cyclohexyl dioxane has the general formula

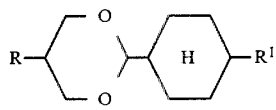

where R and R$^1$ can typically be the same or different straight chain alkyl or alkoxy. These compounds can be prepared as follows:

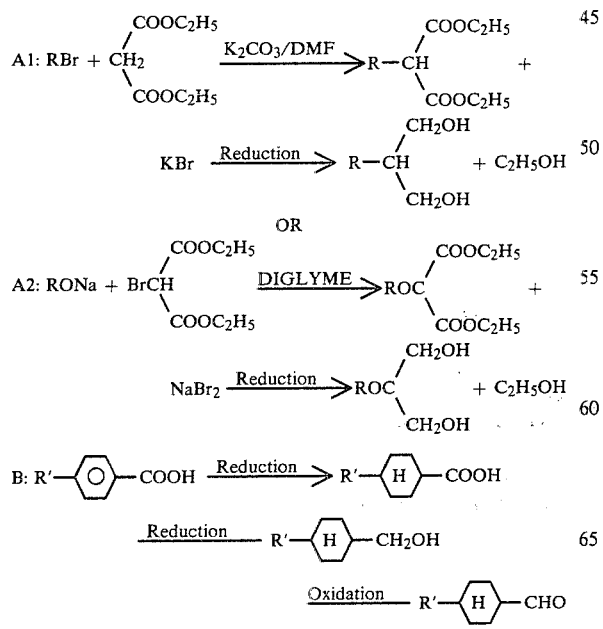

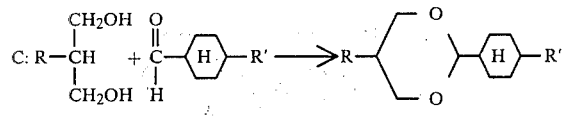

These compounds are described more fully in co-pending U.S. application No. 135,381 filed Mar. 28, 1980, now U.S. Pat. No. 4,298,528.

The cyclohexyl cyclohexyl dioxane compounds

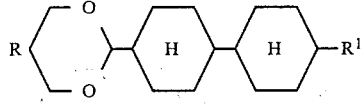

are described in detail in a copending U.S. patent application entitled "Cyclohexyl Cyclohexyl Dioxane Liquid Crystal Compounds and Admixture Containing Same" of common inventorship and assignee herewith. A typical synthesis of these compounds involves steps A(1) or A(2) set forth hereinabove with respect to the cyclohexyl dioxanes, and further steps as follows:

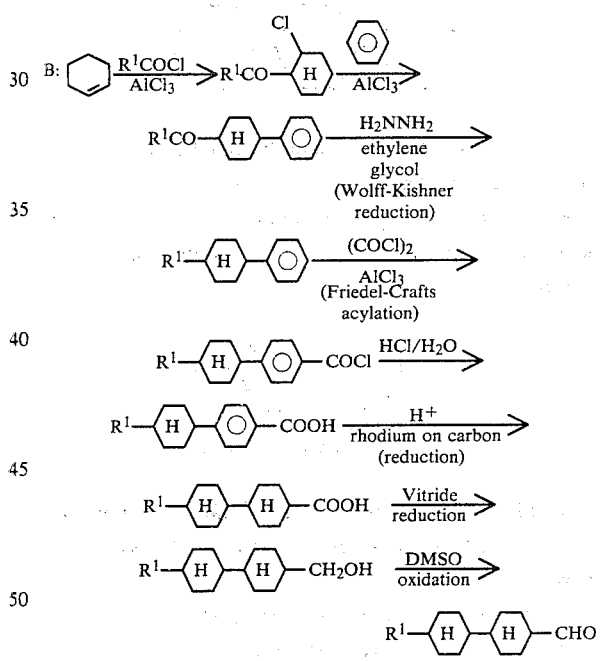

While the invention has been explained by a detailed description of specific embodiments, it is understood that various modifications can be made in them within the scope of the appended claims which are intended to include equivalents of such emobidments.

I claim:

1. A compound of the formula:

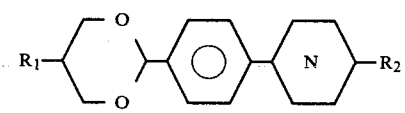

where $R_1$ is alkyl or alkoxy and $R_2$ is alkyl or alkoxy and where ring N is a benzene or a saturated cyclohexane ring.

2. A liquid crystalline compound of the formula:

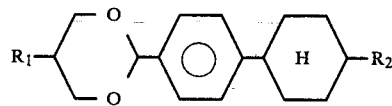

where $R_1$ and $R_2$ independently can be the same or different alkyl group or alkoxy group.

3. A liquid crystalline compound of the formula:

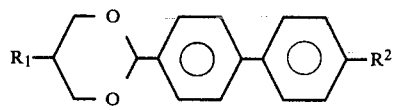

where $R_1$ and $R_2$ independently can be the same or different alkyl group or alkoxy group.

4. A nematic liquid crystal admixture comprising at least about 30 weight percent of a compound of the formula:

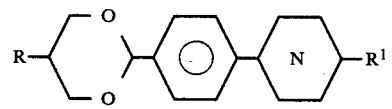

where $R_1$ is alkyl or alkoxy and $R_2$ is alkyl or alkoxy and where ring N is a benzene or a saturated cyclohexane ring.

5. A nematic liquid crystal mixture comprising at least one compound of the formula:

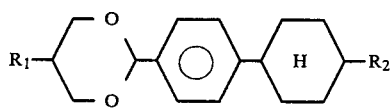

where $R_1$ and $R_2$ independently can be the same or different alkyl group or alkoxy group
and further comprising at least one compound of the formula (a):

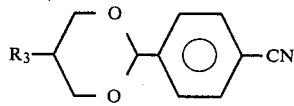

where $R_3$ is an alkyl group or alkoxy group, or of the formula (b):

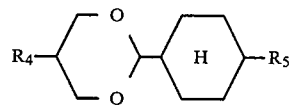

where $R_4$ and $R_5$ independently can be the same or different alkyl group or alkoxy group, or of the formula (c):

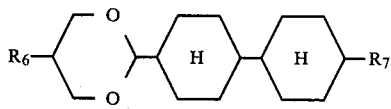

where $R_6$ and $R_7$ independently can be the same or different alkyl group or alkoxy group.

6. A nematic liquid crystal admixture comprising at least about 30 weight percent of a compound of the formula:

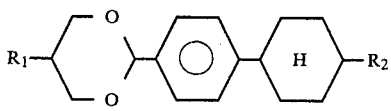

where $R_1$ and $R_2$ can be the same or different alkyl or alkoxy, and comprising at least about 30 weight percent of a compound of the formula:

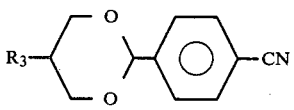

where $R_3$ is an alkyl or alkoxy group, and further comprising at least about 20 weight percent of a compound of the formula:

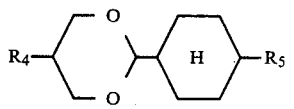

where $R_4$ and $R_5$ can be the same or different alkyl or alkoxy group.

7. An electrooptical display containing the compound claimed in claim 2 or 3.

8. An electrooptical display containing the nematic liquid crystal mixture claimed in claim 5 or 6.

9. An electrooptical display containing the compound claimed in claim 1.

* * * * *